US006518584B1

(12) United States Patent
Woodruff

(10) Patent No.: US 6,518,584 B1
(45) Date of Patent: Feb. 11, 2003

(54) SYSTEM AND METHOD FOR CHARACTERIZING TARGETS USING TWO FORMS OF OPTICAL IRRADIATION AND ACOUSTIC IRRADIATION

(76) Inventor: James Woodruff, 5318 Lakewood Rd., Rootstown, OH (US) 44266

( * ) Notice: Subject to any disclaimer, the term of this patent is extended or adjusted under 35 U.S.C. 154(b) by 0 days.

(21) Appl. No.: 09/695,386

(22) Filed: Oct. 25, 2000

Related U.S. Application Data

(60) Provisional application No. 60/161,412, filed on Oct. 25, 1999.

(51) Int. Cl.[7] .............................. G01J 3/433; G01J 3/00
(52) U.S. Cl. ............................... 250/504 H; 250/494.1
(58) Field of Search .................................. 250/372, 306, 250/504 H, 349, 350, 351, 493.1, 494.1, 504 R; 356/349; 73/572, 659

(56) References Cited

U.S. PATENT DOCUMENTS

| | | | |
|---|---|---|---|
| 4,689,482 A | * 8/1987 | Horikawa et al. | 250/205 |
| 5,045,669 A | * 9/1991 | Ortiz et al. | 219/121.83 |
| 5,257,544 A | * 11/1993 | Khuri-Yakub et al. | 73/643 |
| 5,416,582 A | 5/1995 | Knutson et al. | |
| 5,565,982 A | * 10/1996 | Lee et al. | 356/317 |
| 5,616,826 A | * 4/1997 | Pellaux et al. | 73/24.02 |
| 5,679,899 A | * 10/1997 | Webster et al. | 73/656 |
| 6,081,481 A | * 6/2000 | Sabatier et al. | 367/8 |
| 6,089,094 A | * 7/2000 | Zeng et al. | 73/579 |

* cited by examiner

Primary Examiner—John R. Lee
Assistant Examiner—David A Vanore
(74) Attorney, Agent, or Firm—Birch, Stewart, Kolasch & Birch, LLP

(57) ABSTRACT

An apparatus and process integrates plural sources to irradiate a region and detect, as well as characterize, present chemical or biological agents based on returned signals. The apparatus and process integrate spectroscopy, spectroscopic acoustic interferometry, and swept frequency acoustic interferometry to instigate and detect changes in irradiated chemical and biological agents. A system integrates a tunable wavelength laser with a moderately fixed wavelength laser and an acoustic generator to simultaneously irradiate a region that is to be monitored for chemical or biological agents. Such a system is used to generate databases of response profiles for chemical and biological agents. Such a system is also used with an already obtained database of response profiles and optimization or artificial intelligence routines to identify targets of unknown nature.

18 Claims, 4 Drawing Sheets

SYSTEM AND METHOD FOR CHARACTERIZING TARGETS USING TWO FORMS OF OPTICAL IRRADIATION AND ACOUSTIC IRRADIATION

CROSS REFERENCE TO RELATED APPLICATION

This application claims priority under 35 U.S.C. § 119(e) of U.S. Provisional application No. 60/161,412 filed on Oct. 25th, 1999, the entire contents of which are incorporated herein by reference.

FIELD OF THE INVENTION

The present invention relates to a technique for using multiple irradiation sources to detect and characterize chemical and biological agents.

DESCRIPTION OF THE RELATED ART

Various techniques have previously been considered for detecting illegal and dangerous items, such as drugs, explosives, weapons, and the chemical and biological substances/agents within such items, for implementing crime prevention, police officer protection, security, and counter-terrorism initiatives. In the case of detecting certain types of chemical and biological substances, some known techniques require taking a physical sample of a substance, chemically breaking down (e.g., "cooking") the substance to measure physical characteristics thereof, and comparing the measured physical characteristics with those of reference substances. Such invasive detection techniques create a likelihood of endangering personnel through exposure to hazards while retrieving the substance to be analyzed, and are slow and limited in terms of detection capability because only physically retrievable substances can be analyzed. Another known detection technique employs spectroscopy, using non-hardened $CO_2$ lasers and the like, to optically detect or characterize substances. This technique also has drawbacks, however, because the requisite lasers are large and expensive. Furthermore, the inventor of this application has found that, although a generally accurate technique for characterizing substances/agents, laser spectroscopy in some instances will fail to recognize subtle differences between the makeup of substances/agents, thereby failing to ensure against false alarms and errors.

SUMMARY OF THE INVENTION

This invention presents an approach that integrates three or more sources having different nature to irradiate a region and detect, as well as characterize, present chemical or biological agents based on returned signals. More particularly, the present approach integrates spectroscopy, spectroscopic acoustic interferometry, and swept frequency acoustic interferometry to instigate and detect physical and mass changes in irradiated chemical and biological agents. In its most basic level, the inventive approach integrates a tunable wavelength laser with a moderately fixed wavelength laser and an acoustic generator to simultaneously irradiate a region that is to be monitored for chemical or biological agents. Such a system is used to generate databases of response profiles for chemical and biological agents. Such a system is also used with an already obtained database of response profiles and optimization or artificial intelligence routines to identify targets of unknown nature.

The inventive approach has the advantage of enhanced signal discrimination because of the differing response of different chemicals and biological agents to multiple simultaneous irradiations. The response profile, as a function of frequencies of the three simultaneous irradiations, facilitates discrimination between related but different chemical and biological agents. Also, since the irradiations can be directed to distant regions and the return signal detected from these distant regions, the present approach has the advantage of keeping the system operator safe from unnecessary exposure to potentially unsafe chemical or biological agents.

BRIEF DESCRIPTION OF THE DRAWINGS

Other aspects and advantages of the present invention will become apparent upon reading the detailed description and upon reference to the drawings in which.

DETAILED DESCRIPTION

An exemplary embodiment of the invention integrates three different sources to irradiate a region and detect, as well as characterize, chemical or biological agents present in the irradiated region based on returned signals. In this embodiment, spectroscopy, spectroscopic acoustic interferometry, and swept frequency acoustic interferometry are used to instigate and detect physical and mass changes in irradiated chemical and biological agents. The embodiment integrates a tunable wavelength laser with a moderately fixed wavelength laser and an acoustic generator as the three irradiation sources that are used to monitor a region for chemical or biological agents.

Figure 1:
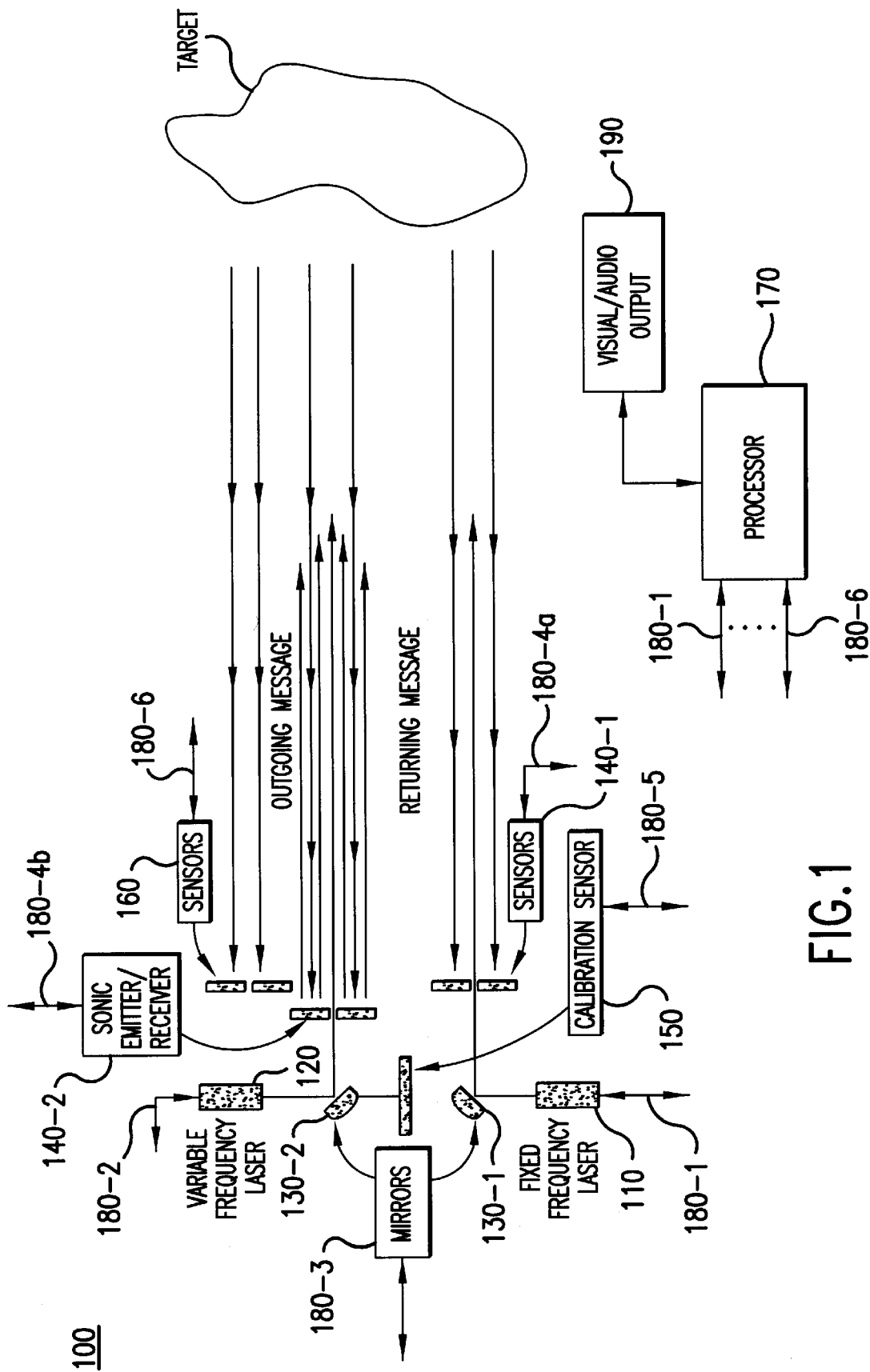
FIG. 1 is a general block diagram illustrating an exemplary embodiment of an integrated chemical or biological detection system according to the present invention.

FIG. 1 is a general block diagram illustrating an exemplary embodiment of an integrated chemical or biological detection system 100. As shown, the detection system 100 includes a fixed frequency laser 110, a variable frequency laser 120, sonic emitters/receivers 140-1 and 1402, and a controller/processor 170 that includes memory. The exemplary embodiment of FIG. 1 also includes mirrors 130-1 and 130-2, laser calibration sensors 150, background sensors 160, and processor output device 190.

In one implementation, the fixed frequency laser 110 is a Nd:YAG laser, which is capable of being operated at one of a small number of laser wavelengths at about 1.06 micron. Second and third harmonic generating crystals are used to obtain the double and triple (half and third wavelengths, respectively) of the Nd:YAG laser Infrared irradiations. Consequently, what is meant by a fixed frequency laser is a laser that is capable of being operated at one of a small number of laser wavelengths. Of course other lasers may be used to implement the fixed frequency laser without departing from the spirit of the invention. For example, the fixed frequency laser may be implemented as a system using a compact solid state laser generating 0.63 $\mu$m along with second and third harmonic generation, or may be implemented as a system using semiconductor lasers. The fixed frequency laser beam is directed by a mirror 130-1 to go through a sonic emitter/receiver 140-1 and onto a target (which may be gaseous, liquid, or solid). The mirror 130-1 includes all of the optics necessary—and can be implemented using mirrors as well as lenses—to shape, collimate, and direct the fixed frequency laser beam. The mirror 130-1 allows a small fraction of the energy of the fixed frequency laser beam to be directed towards calibration sensors 150.

In one implementation, the variable frequency laser 120 is a compact solid state laser such as Alexandrite, allowing wavelengths in the range of 0.2–1.75 microns. The variable frequency laser 120 is capable of being operated at one of a large number of laser frequencies. The variable frequency laser beam is directed by a mirror 130-2 to go through the sonic emitter/receiver 140-2 and onto the target. The mirror 130-2 includes all of the optics necessary—and can be implemented using mirrors as well as lenses—to shape, collimate, and direct the variable frequency laser beam. The mirror 130-2 allows a small fraction of the energy of the variable frequency laser beam to be directed towards calibration sensors 150. The frequency of the irradiation generated by the variable frequency laser beam is adjusted based on the signal returned from the target so as to optimize the return signal with a view for better identifying the chemical or biological agent being irradiated. In one implementation, the variable frequency laser 120 is pulsed and has a pulse length (with a range of subnanoseconds to several tens of nanoseconds) that is shorter than that of the fixed frequency laser. The choice of laser pulse lengths is driven by the need for optimizing and enhancing the distinguishing features of the measured response profiles. The choice of repetition rates and pulse lengths for the fixed frequency laser 110 and variable frequency laser 120 must abide by allowing the two laser irradiations to overlap in time and space at the target. Mirrors 130-1 and 130-2 also include (e.g., by attachment to their backside) wavelength/frequency discriminating elements (e.g., an optical grating and/or filters) that enable the separating (and therefore the identifying) of different incident optical wavelengths for the laser irradiations.

The calibration sensors 150 separately measure the fractions of the laser energy of the fixed and variable frequency laser beams being irradiated onto a target. The calibration sensors 150 can also measure the frequencies of the laser irradiations. The calibration sensors 150 also measure the repetition rate of the laser irradiations. These measurements provide information necessary for the proper operation of the controller/processor 170 and, thus, the proper operation of the detection system 100. In another implementation, the calibration sensors 150 actually represent nonintegrated calibration sensors separately dedicated to the fixed frequency laser 110 and variable frequency laser 120 and providing their measured information to the controller/processor 170.

The sonic emitter/receivers 140-1 and 140-2 generate sonic energy that is then directed onto the target. The sonic emitter/receivers 140-1 and 140-2 include the transducers used to generate the emitted sonic energy and detect the received sonic energy. At least one sonic transducer, connected to a sweep generator (e.g., covering sonic and ultrasonic spectral ranges) is used to generate the emitted sonic energy—in this disclosure, "sonic" is used to refer to acoustic regardless of its specific frequency or spectral range. And at least one sonic transducer, connected to a tunable receiver, is used detect the received sonic energy resulting from the target's reaction to the sonic and laser energies and from background effects. The two sonic transducers form a sweep frequency acoustic interferometer or an ultrasonic interferometer. In one implementation, a pellicle emitter/receiver (not shown in FIG. 1) is used to direct the sonic energy onto the target. A material is used that transmits the laser frequencies but that responds to the sweep generator and generates the sonic frequencies (this material detects returned sonic irradiation by absorbing it). The pellicle emitter/receiver therefore enables the spatial coexistence of the optical and sonic irradiations. In another implementation, a material that responds to the sweep generator and generates the sonic irradiation (and detects the returned sonic irradiation by absorbing it) but that reflects the optical irradiation is used as emitter/transmitter. In another implementation, a material that reflects both sonic and optical irradiations is used as the transmitter/receiver.

The sonic emitter/receivers 140-1 and 140-2, the calibration sensors 150, and the background sensors 160 each also include light detectors that detect laser energy returned to the detection system 100. In one implementation, the light detectors are photo-detectors or CCD arrays using semiconducting or solid state material. The light detectors generate signals corresponding to the irradiation returned to the system as a result of fluorescence and mass change of the chemical or biological agents being irradiated. The light detectors also measure background effects. The generated signals indicate the amount as well as wavelength of the detected optical energy—e.g., using optical gratings and/or filters to separate different returned optical wavelengths.

The detection system 100 also includes a controller/processor 170. The controller/processor 170 includes at least one amplifier, memory, and a processor. In one implementation, the amplifier is lock-in based and is tunable to the different repetition rates of the three irradiation sources. This amplifier, therefore, can amplify a returned signal having a specific repetition rate with rather good signal to noise ratio. In another implementation, the system has at least one amplifier dedicated to the fixed frequency laser 110, at least one amplifier dedicated to the variable frequency laser 120, and at least one amplifier dedicated to the acoustic generator. The three irradiation sources may use different pulse repetition rates so that the signals generated by the different irradiations are detected using the lock-in amplifier(s) without contaminating each other, thus allowing separate and enhanced processing.

The controller/processor 170 processes information generated by the various elements of the detection system 100, including calibration data, emitted optical and sonic energies and frequencies, and returned optical and sonic energies and frequencies. The controller/processor 170 also controls the operation of the overall system 100, including the varying of the frequencies of the fixed and variable frequency lasers and the acoustic energy. The controller/processor 170 accomplishes its controlling task using a feedback of the signals (communicated from the sensors to the controller/processor 170 by communications links 180-1, ..., 180-6) representing the operation of the various elements of system 100 and representing signals returned from the target to optimize the performance of the detection system 100 in characterizing or identifying the chemical or biological nature of the target. The controller/processor 170 includes the memory necessary (e.g., RAM dynamically used in processing information, longer term memory used in storing new information for later use, and ROM containing the controlling/processing information databases and programs) and a CPU to accomplish its controlling and processing tasks. The controller/processor 170 may be local or remote.

If the detection system 100 is implemented as a self-sufficient portable system, then the controller/processor 170 is integrated within the detection system 100 with communication links 180 being hardwired (electronic or optical) or wireless. If the detection system 100 is implemented as a terminal controlled by a central location, then the controller/processor 170 may be located remote from the rest of the elements of the detection system 100. In the remote detection system 100 implementation, the detection system 100 and the central controller/processor 170 communicate through wireless or hardwired means—the latter including cable, telephonic, modem, and optical fiber communication.

The detection system 100 includes an output terminal 190 that outputs the results of the characterization or identification of the chemical/biological nature of the target. In one implementation, the output terminal is a printer that prints out the results or is a screen monitor (e.g., a touch-pad or CCD display)that displays the results. The output terminal may be implemented as integrated within the detection system 100 for a self-sufficient portable system. On the other hand, the output terminal 190 may be implemented as located at the central location controlling a detection system 100 implemented as a remote system. In other implementation, the output terminal 190 includes audio signals generating devices (e.g., tone generator or voice synthesizer) that can communicate the findings of the controller/processor 170 to operators (e.g., generating alarm signals). Another implementation of the output terminal 190 combines any two of the video, audio, and printing functions. Another implementation of the output terminal 190 combines video, audio, and printing functions.

Figure 2:
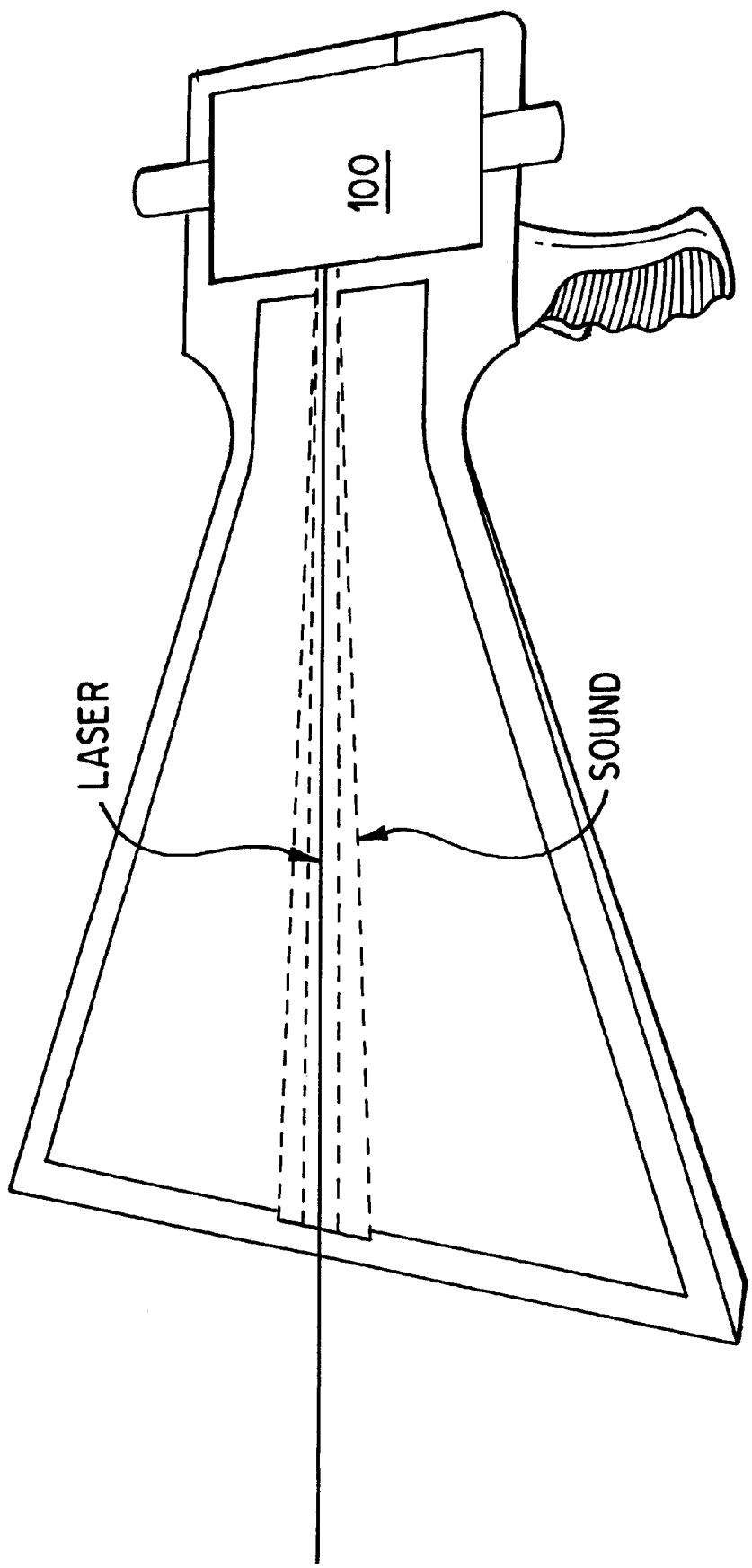
FIG. 2 is a diagram showing a housing shape and partial makeup of a hand-held detection system according to an embodiment of the present invention.

The detection system can be implemented as a handheld system. FIG. 2 shows a cut-away view of a housing shape and partial makeup of a hand-held detection system according to the present invention. As shown in FIG. 2, the housing shape is essentially conic (e.g., a horn; but other shapes can be used) that may be coated on the inside with a highly reflecting material to enhance the detection of signals returned from distant targets. In another implementation, the inside coating can be made to absorb stray and undesirable optical irradiations not representing returns from a target. The detection system can be implemented as a robot-carried mobile system. The detection system can also be implemented as a stationary system.

Having described physical configurations of detection systems according to the present invention, we next describe the operation and use of detection systems according to the present invention.

Any material has a molecular structure and, therefore, responds to optical and sonic probes: this response is unique to the material and the probe used. When irradiation interacts with the molecules, the population of energy levels is affected. Over time, the variously excited or populated energy levels relax back to their original ambient energy levels and populations. The return of molecules to ambient conditions is accompanied by emitting the energy they absorbed when excited. The emitted energy, when a molecule relaxes, includes photons (as in fluorescence) and phonons (as in a shift in the frequency of reflected optical and acoustic irradiation).

Responding to acoustic irradiation, the molecular levels change their population as they are excited and relaxed. The profiles of excitation and relaxation depend on the frequency content of the acoustic energy pulse and the molecular structure of the target being irradiated. The attenuation and speed of propagation of an acoustic irradiation also depends on the acoustic frequency and target material.

Responding to optical irradiation, the molecular levels also change their population—although in a different manner than the change due to acoustic irradiation—as they are excited and relaxed. The profiles of excitation and relaxation depend on the frequency content of the optical irradiation and the molecular structure of the target being irradiated. The excitation and relaxation demonstrates itself through the fluorescence resulting from the molecules.

In the embodiment schematically shown in FIG. 1, the invention uses the simultaneous interaction of three irradiations, coexisting in time and space, to acquire and identify a profile unique to the molecular structure of a target and the specific frequencies/wavelengths of the exciting/probing irradiations. The three irradiations are obtained from two lasers and an acoustic generator. The coexistence in time and space of the three irradiations influence the profile of the excited energy levels and their populations in a manner unique to the specifics of the three irradiations and the nature of the molecular structure of the irradiated target; a manner different in nature than when one or two irradiations are present instead of three. Energy levels in molecules excite, populate, and relax differently depending on the number of different irradiations used. Consequently, energy returned (optical and acoustic) by a target illuminated by the three irradiations provides information reflecting the unique profile of the excited energy levels of the molecular structure of the target and, therefore, provides information that uniquely characterizes and identifies the nature of the target. The advantage obtained from using three irradiations is the ability to finely tune the probing of a target's molecular energy levels and, therefore, the ability to better distinguish between targets having different but related molecular structures. Moreover, using irradiations having different nature assures the detection of some information, as well as enhancing the amount of information obtained, about the target's nature. For example, an operator of a detection system according to the present invention still has the opportunity to acquire information about a specific target even if the target does not have a strong response to any one, or two, irradiation type used by the detection system according to the present invention.

Figure 3:
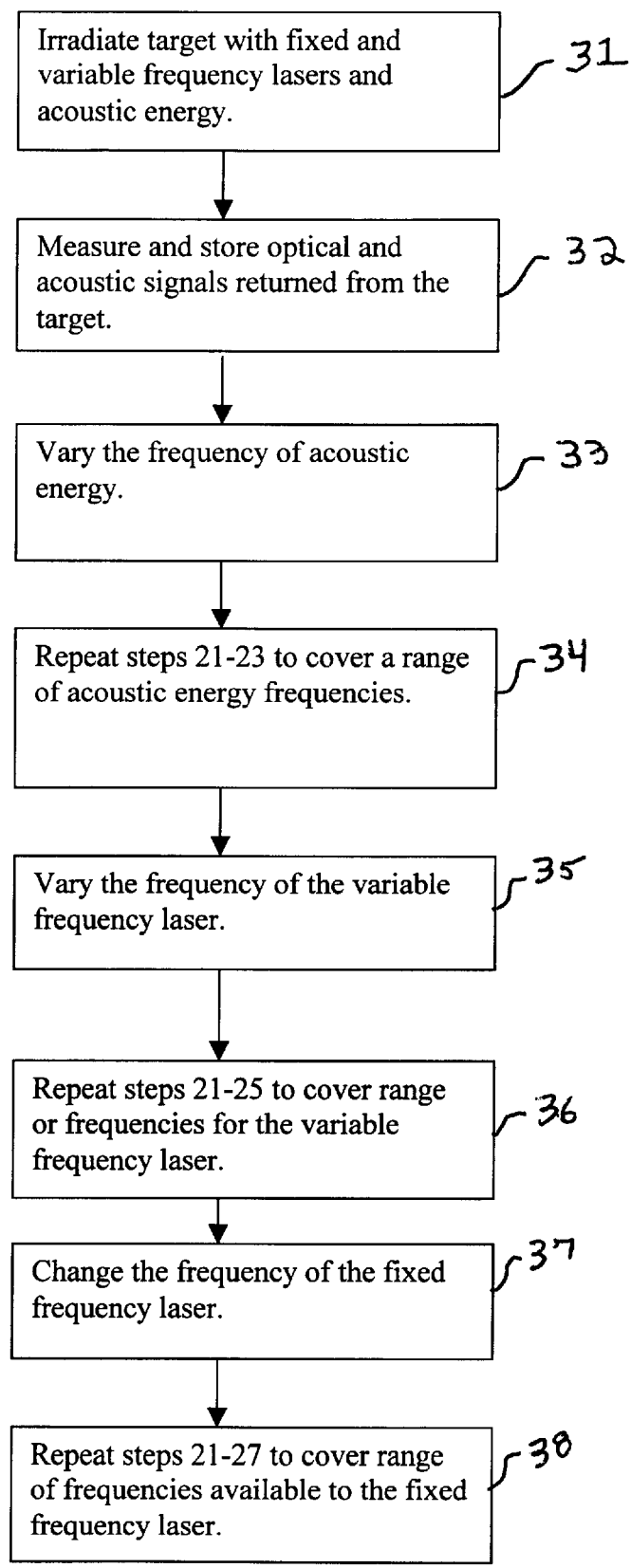
FIG. 3 is a general flow diagram illustrating a method of using the present invention to generate a database of identifying response profiles for chemical and biological agents.

FIG. 3 s hows a flow diagram for using the embodiment of the invention shown in FIG. 1 to build a database of the unique response profiles of different chemical and biological agents. A target is irradiated with specific frequencies of fixed and variable frequency lasers and acoustic energy (step 31). The optical and acoustic signals (including information about intensity and frequency) returned from the target are measured and stored (step 32). The frequency of the acoustic energy is varied (step 33). Steps 31–33 are repeated until the range of available acoustic frequencies is covered (step 34). The frequency of the variable frequency laser is varied (step 35). Steps 31–35 are repeated until the range of frequencies available for the variable frequency laser is covered (step 36). The frequency of the fixed frequency laser is changed (step 37). Steps 31–37 are repeated until the range of frequencies available for the fixed frequency laser is covered (step 38). At the end of this iterative process, the accumulated information provides the unique profile of the target material's response to the irradiations used.

The database of response profiles for chemical and biological agents has information on their dependence on temperature and pressure. The background ambient temperature and pressure are obtained using the background sensors 160. The acoustic irradiation is especially valuable in providing these measurements since sound's speed depends on the temperature and the pressure of the medium in which it travels. Temperature and pressure are additional characterizing parameters for distinguishing between the response profiles of different chemical and biological agents.

Figure 4:
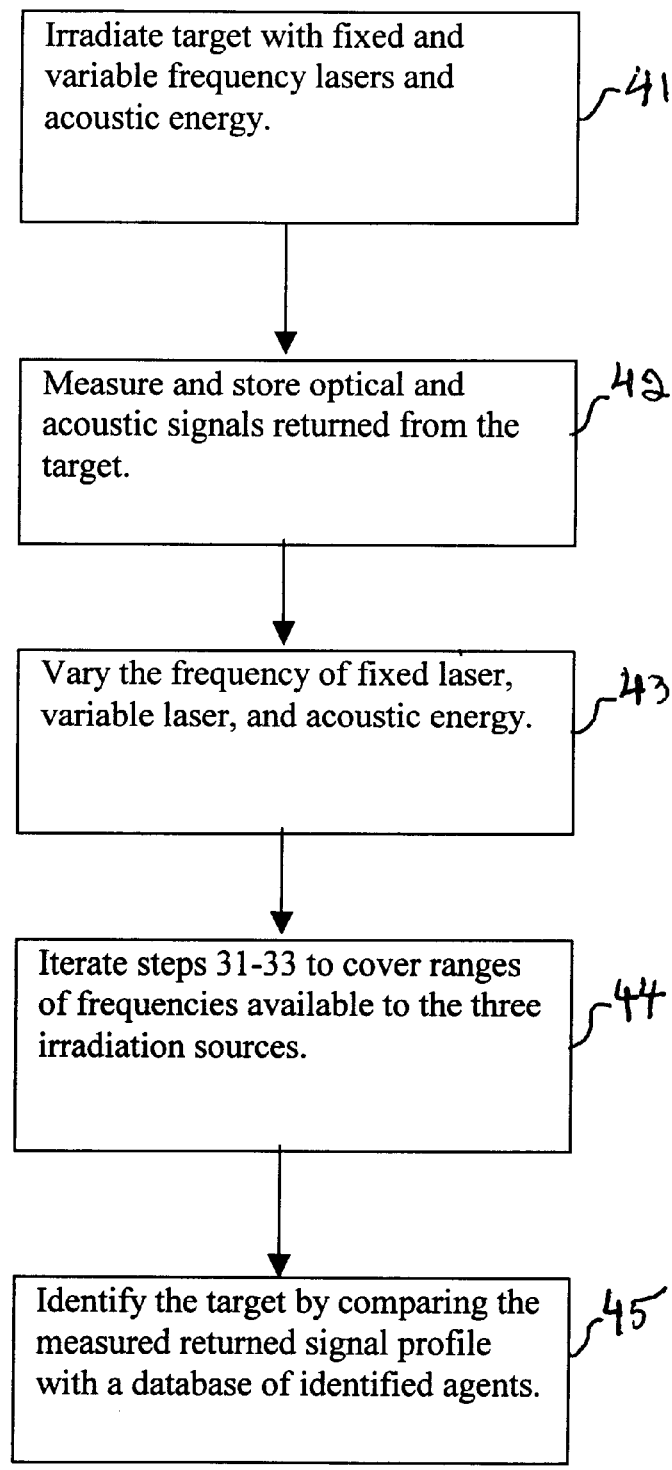
FIG. 4 is a general flow diagram illustrating a method for using the invention to identify an unknown target by comparing its response profile to specific response profiles in a database.

FIG. 4 shows a flow diagram for using the embodiment of the invention shown in FIG. 1 to identify a target by comparing its response profile to a database of response profiles of different chemical and biological agents. A target is irradiated with specific frequencies of fixed and variable frequency lasers and acoustic energy (step 41). The optical and acoustic signals (including information about intensity and frequency) returned from the target are measured and stored (step 42). The frequency of the fixed and variable lasers and acoustic energy is individually varied (step 43). Steps 41–43 are iterated to cover the range of frequencies available to the three irradiations (step 44). In one exemplary embodiment, artificial intelligence, optimization, or both, are used to identify the target by comparing the obtained response profile of the target with a database of characterized chemical and biological agents (step 45). Artificial intelligence, optimization, or both, is used to avoid unnecessarily varying the frequencies of the three irradiations over all of the available ranges. For example, an optimization process is used that first identifies a specific response peak for the unknown target; the process then identifies chemical and biological agents in the database that have the same (within experimental uncertainties) response peak; the process then limits the frequencies of the three irradiations to be near those for the other response peaks of the identified agents. This optimization process iterates the peak-identification and frequency-limitation steps and thus very quickly zeros in on the identity of the unknown target.

A specific chemical or biological agent is used for calibrating the detection system 100. The choice of the calibration agent depends on the operative frequency ranges of the various irradiations. In one implementation, a chemical or biological agent having a strong response to a limited number of frequencies of irradiations is used as the calibration source. Preferably the calibration agent has a response profile that is generally temperature and pressure insensitive. Other approaches can be used to choose the calibration agent without departing from the spirit of the invention.

Although the inventive approach described above showed implementations using three irradiations (fixed frequency laser, variable frequency laser, and acoustic energy), the principles of the invention can be implemented using more than three irradiations. For example, in another embodiment, a submillimeter or millimeter irradiation source, or both, is used—together with or instead of the fixed and variable frequency lasers—to map out the response profiles of chemical and biological agents to frequencies in these electromagnetic spectra. The vibrational and rotational energy levels of molecules are responsive to excitations by irradiations in the submillimeter and millimeter spectra. Using additional irradiation spectra enhances the ability of a detection system according to this invention to distinguish between different chemical and biological agents.

In another embodiment, a non-contact detection system as described above (using optical and sonic irradiations to detect, characterize, and identify targets and implemented as a handheld, a robot-carried, or a stationary system) is further enhanced by adding contact-based thermal and electrical conductivity sensors. For example, electrical or electronic circuits having micro-grown isolated and interlaced voltage electrodes and thermal sensors in the from of a two dimensional array of pixels can be attached to the optical/sonic detection system (thus forming an overall target detection system) thus enabling the further acquisition of contact-based characterizing/identifying information about the nature of the target material. The interlaced and isolated voltage electrodes allow the measuring of the electrical conductivity of a target when it touches the electrodes. The thermal detectors, on the other hand, allow the measuring of the thermal coefficient of a touching target as it is heated by the electrical current passing through it. The contact-based sensors can be implemented so that the electrodes can be charged to a voltage determinable by a user. The contact-based detection electrical circuits can be implemented using semiconductors and/or insulating glass materials and substrates in the form of integrated or non-integrated circuits.

In another embodiment, a detection system according to this invention is used in combination with others of its kind, or other kinds, to provide more extensive spatial and database coverage. A central controller/processor 170, with extensive computing and storing resources, is used in implementations requiring extensive databases or plural cooperating systems to cover a region.

The above-described detection system may be implemented in a device having a plurality of operation modes, such as: a Power Off Mode, an Off mode, a Stand-By mode, a Manual Self Test mode, a Visual Reference Data mode, and a Visual Aperture Test mode. The user may select between these various operating modes, for example via a graphical user interface or touch-panel display. The various operating modes may have the following characteristics:

In the Power Off mode, there is no power available anywhere within the system (i.e., the system is totally dormant), whereas, in the Off mode, power is provided to the detection unit for the optical sensors, lasers, sonic emitter receivers, and the contact-based detection circuitry. In the Off mode, if a target substance lands within the contact-based detection area, the contact detection unit recognizes the existence of a target and initiates system reboot, thereby allowing identification to be carried out. Naturally, rebooting the system would result in delays, for example due to the execution of calibration and diagnostic sequences.

In the Stand-By mode, power is provided to every element of the system. While in Stand-By mode, the system may cycle between built in test (e.g., diagnostic) and calibration sequences to ensure that the system is fully prepared to reliably execute identification once the operator returns the system to active operation. The system will not output alarms during the Stand-By mode, but will aurally or visually alert the operator to the existence of a questionable material present in the system. When the operator selects the Manual Self Test mode, the system immediately initiates and completes test and calibration sequences to ensure proper subsequent operation.

In the Visual Reference Data mode, the system operator is enabled to interactively view various stored reference profiles and visually compare such reference profiles with the measured data for the irradiated agent/substance. This particular operating mode may be valuable for the operator when novel agents/substances begin to appear that do not quite match the profile of any agent/substance stored in the database. This visual reference gives the user an opportunity to determine the agent's/substance's likely make-up and probable characteristics. Furthermore, when the detection system is exposed to an agent whose characteristic response profile is not part of the database in the system (but is an agent known to the operator/user), this mode can be used to actively perform an educational function whereby the operator/user interactively enhances the database of the system by adding the newly measured response profile of the heretofore uncharacterized agent to the data base of the system. Finally, in the Visual Aperture Test mode, a visual display of the detection aperture area is output to the user (e.g., by outputting CCD imaging signals of the internal detection system to the user display), thereby allowing the system operator to visualize the current condition of the detection aperture area and thereby determine whether cleaning or some other type of maintenance is required. Having described various operating modes, it should be apparent to those skilled in the art that various other operating modes may be implemented in the detection system disclosed herein.

A detection system according to the present invention can be used to characterize, recognize, and identify chemical and biological ingredients and agents of contraband, limited, regulated, and unregulated nature including but, not limited to, drugs, narcotics, explosives, concealed and unconcealed weapons, toxins, poisons, and pollutants. Such a system can provide environment and system control, audible and visual alarms, and system status information at remote, local, and central, locations.

Although the present invention has been described in considerable detail with reference to certain embodiments, it should be apparent that various modifications and applications of the present invention may be realized without departing from the scope and spirit of the invention. Scope of the invention is meant to be limited only by the claims presented herein.

I claim:

1. A system for characterizing a target, said system comprising:
    a first laser capable of outputting a first number of laser frequencies and having a first repetition rate;
    a second laser capable of outputting a second number of laser frequencies and having a second repetition rate, said second number being greater than said first number;
    an acoustic sweep frequency generator capable of outputting a range of sonic frequencies and having a third repetition rate;
    a measurement sensor receiving sonic and laser irradiations returned from the target irradiated by said first laser, second laser, and said acoustic generator; and
    a processor operatively connected to said first laser, said second laser, said acoustic sweep frequency generator, and said measurement sensor, said processor controlling the output laser and sonic frequencies, obtaining measurements from said sensor, and characterizing the target based on processing said obtained measurements.

2. The system of claim 1, further comprising:
    a pellcite transmitting portions of the irradiation outputs of said first and second lasers and directing the sonic output of said acoustic generator.

3. The system of claim 2, further comprising:
    a background sensor receiving background return signal of the sonic output, said background sensor being operatively connected to said processor.

4. The system of claim 3, further comprising:
    a calibration sensor receiving portions of the irradiation outputs of said first and said second lasers, said calibration sensor being operatively connected to said processor.

5. The system of claim 4, further comprising:
    at least one lock-in amplifier having an input operatively connected to said background, calibration, and measurement sensors, and having an outout operatively connected to said processor.

6. The system of claim 4, further comprising:
    at least three lock-in amplifiers, each having an input connected to one of said sensors and each having an output connected to said processor.

7. The system of claim 4, wherein said detection system is portable and has said processor integrated locally with other elements of said detection system.

8. The system of claim 4, wherein
    elements of said detection system, other than said processor, are field deployable,
    said processor is centrally located, and
    said operative connection are through a communications link.

9. The system of claim 8, wherein said communications link includes at least on of wireless, telephone, fiber, and cable communication.

10. The system of claim 8, wherein said field-deployable detection system is portable.

11. The system of claim 8, wherein said detection system is hand held.

12. A method of characterizing a target, said method comprising:
    (a) directing a sonic irradiation onto the target;
    (b) directing an irradiation from a first laser onto a target;
    (c) directing an irradiation from a second laser onto the target, wherein the sonic irradiation and the first laser and the second laser irradiations overlap in time and space at the target;
    (d) receiving and measuring a response signal from the target irradiated by the sonic irradiation and the first laser and the second laser irradiations; and
    (e) characterizing the irradiated target based on processing the measured response signals from the target to obtain a response profile of the target.

13. The method of claim 12, further comprising:
    (f) varying the frequency of the sonic irradiation and sequentially repeating (a)–(d) to cover a range of sonic frequencies;
    (g) varying the frequency of the first laser and sequentially repeating (a)–(d) and (f) to cover a range of frequencies for the first laser;
    (h) varying the frequency of the second laser and sequentially repeating (a)–(d), (f), and (g) to cover a range of frequencies for the second laser.

14. The method of claim 13, further comprising:
    receiving and measuring a return signal of the sonic irradiation from the ambient background of the target, thus determining temperature and pressure information of the background, said receiving and measuring a return signal occurring before (a).

15. The method of claim 13, wherein the target is known, and wherein said method further comprises:
    replacing the target with another known target and performing (a)–(h), thus generating a database of response profiles for different known targets.

16. The method of claim 13, wherein the target is unknown, and said characterizing the irradiated target includes comparing the profile of the measured responses of the unknown target with a database of response profiles of known targets.

17. The method of claim 16, further comprising:

limiting the number of iterations of said steps (a)–(d), (f), (g), and (h) by identifying a first response peak for the unknown target, identifying a set of known targets in the database having the identified first response peak of the unknown target, and limiting the iteration of (a)–(d), (f), (g), and (h) to irradiation frequencies near which said set of known targets have other response peaks.

18. The method of claim 15, wherein said known targets include at least one of drugs, explosives, weapons, or toxins.

* * * * *